United States Patent [19]

Martin

[11] Patent Number: 4,971,557
[45] Date of Patent: Nov. 20, 1990

[54] CHEEK RETRACTOR

[75] Inventor: Patrick E. Martin, La Costa, Calif.

[73] Assignee: Johnson & Johnson Consumer Products, Inc., New Brunswick, N.J.

[21] Appl. No.: 422,477

[22] Filed: Oct. 17, 1989

[51] Int. Cl.$^5$ .............................................. A61C 5/00
[52] U.S. Cl. .................................................... 433/140
[58] Field of Search ........................................ 433/140

[56] References Cited

U.S. PATENT DOCUMENTS

| | | | |
|---|---|---|---|
| 903,344 | 11/1908 | Wackler | 433/140 |
| 1,474,497 | 11/1923 | Stolper | 433/140 |
| 2,125,980 | 8/1938 | Basil | 433/140 |

OTHER PUBLICATIONS

"bond-pak" Advertisement, Amer. Journal of Orthodontics, 9-1980, vol. 78, No. 3.

Primary Examiner—John J. Wilson
Attorney, Agent, or Firm—Paul A. Coletti

[57] ABSTRACT

An oval cheek retractor enclosing an oval work area and attached to a handle. The cheek retractor has a pair of lip extenders at either oval end so that the user can either push or pull the cheeks without changing the hand being used.

6 Claims, 2 Drawing Sheets

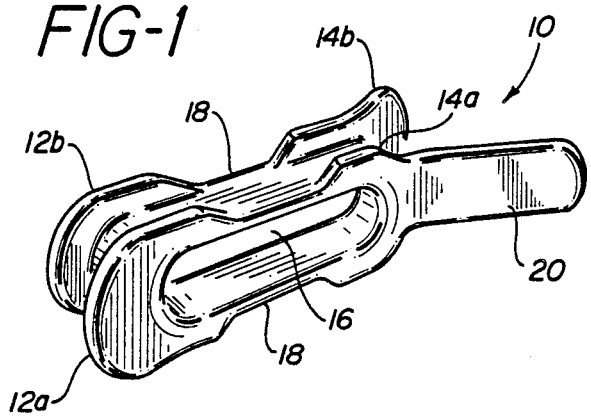
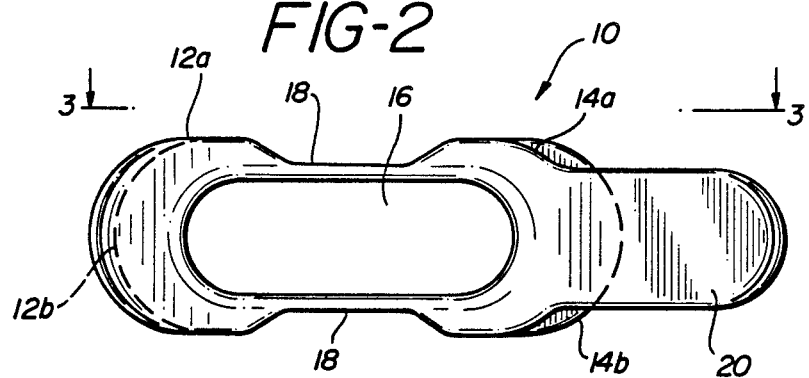
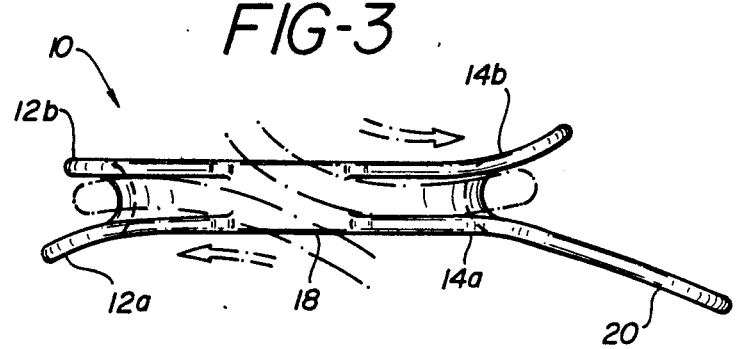

CHEEK RETRACTOR

FIELD OF THE INVENTION

This invention relates generally to cheek retractors for use in orthodontic applications. More specifically, the invention relates to cheek retractors for use in orthodontic bracket applications. Most specifically, the invention relates to cheek retractors for use in applying and debonding dental brackets.

BACKGROUND OF THE INVENTION

In general, cheek retractors have been commonly used in dental procedures. These cheek retractors are a necessity when the oral surgeon or dentist must perform work on teeth toward the rear of the mouth. A cheek retractor is inserted into the mouth to pull the lips and cheek away from the area to be worked. At that point, the dental procedure is possible within the space created by the cheek retractor.

Cheek retractors have, however, had certain natural drawbacks. First, cheek retractors generally fall into one of two categories. Either the cheek retractor is required to be emplaced inside the full mouth to perform a two-handed operation, or the cheek retractor must be held in place on one side of the mouth, removed, and put into the opposite side of the mouth so that the cheek retractor is held in a different position. This second procedure must be done with both hands, so that dental procedures are impossible during shifting. In other words, there have been no uniform, universal cheek retractor useful for oral procedures on either side of the mouth.

Second, the cheek retractors used to simultaneously hold back both sides of the mouth generally have been flimsy and because they pull back both sides, tend not to draw the cheek far enough away from the mouth for proper positioning of the mouth and adequate work clearance.

SUMMARY OF THE INVENTION

It is therefore an object of the invention to provide a cheek retractor capable of being used on either side of the mouth.

It is further an object of the invention to provide a cheek retractor useable as a one-handed device.

It is yet another object of this cheek retractor to allow the user to either retract the cheek through a pushing or a pulling motion.

It is yet another aspect of the invention to provide a cheek retractor which increases the area of the mouth in which oral surgery can be performed.

Finally, it is an object of the present invention to provide a cheek retractor wherein the retractor is made from a rigid yet autoclavable material.

These and other objects of the invention are seen in the cheek retractor which has a generally oval shape and has a handle projecting to one side. The retractor contains a pair of channeled edges into which can be inserted the lips of the patient. Thus, the user can either pull or push the retractor in order to expose the desired side of the mouth, making the present retractor a one-handed device.

These and other aspects of the present invention will be better understood from the attached detailed description of the drawings as well as the detailed description of the invention in which:

DETAILED DESCRIPTION OF THE DRAWINGS

FIG. 1 is a perspective view of a preferred embodiment of the invention;

FIG. 2 is a top elevation view of a preferred embodiment of the invention;

FIG. 3 is a side plan view of the invention seen along lines 3—3 of FIG. 2; and

DETAILED DESCRIPTION OF THE INVENTION

Figure 4:
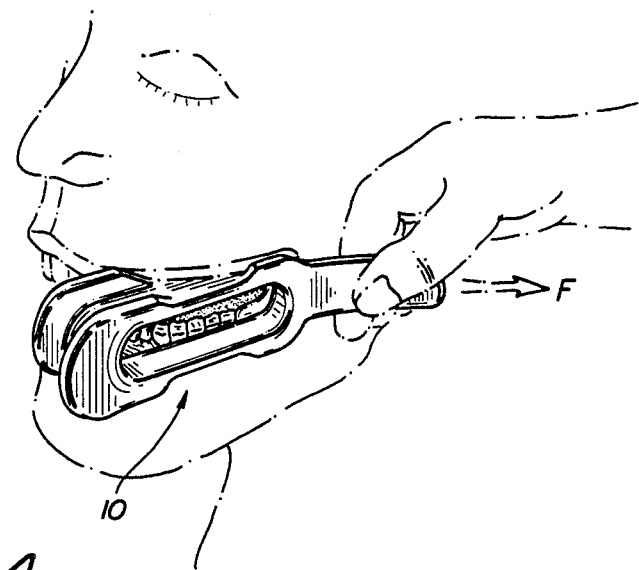
FIG. 4 is a perspective view of the cheek retractor as used in the patient's mouth.

As seen in FIGS. 1 through 4, the invention comprises a cheek retractor 10 having dual-sided lip extenders 12, 14, and an opening 16 through which oral surgery can be performed. The cheek retractor 10 is generally oval in shape. Each of the lip extenders or holders 12, 14 are at the rounded ends of the retractor 10 and have a pair of edges 12a, 12b and 14a, 14b respectively. Each double sided edge 12, 14 is connected by a bridge 18 to form oval opening 16.

The handle 20 can be pushed using force F, to exert lip extender 14 against the lip, causing the oval opening or work area 16 to expose the teeth toward the back of the mouth, as seen in FIG. 4. Conversely, the opposite lip extender 12 can be placed against the lip and the handle 20 can be pulled, so that the opening 16 exposes the opposite side of the mouth through cheek retractor 10. The upper edge of the retractor 10 formed by surfaces 12a, 18, 14a also helps protect the lips and gums from scalpels, drills, burns or other abrasive tools during use.

In this way the cheek retractor 10 operates as a one-hand device. The user can hold the cheek retractor 10 (which is generally formed from a rigid and autoclavable material) at the handle 20. Edges 12a, 12b or 14a, 14b of cheek retractor 10 fit about the desired lip. Then, the user pushes or pulls the cheek retractor 10, dependent upon which part of the mouth is being worked.

The retractor of the present invention works especially well when using devices in which the user may want to operate with a dominant hand, such as drills, scalpels, or debonding devices, or any other like instrument.

The invention has been disclosed in conjunction with a presently preferred embodiment but it is intended that the invention be determined from the scope of the appended claims and their equivalents.

What is claimed is:

1. A cheek retractor comprising a lip extender having two ends surrounding an work area and a handle attached to the lip extender, said retractor engageable with the lips at the lip extender such that by pushing or pulling the handle, the lip extender will force a cheek away from the mouth to expose the teeth at the work are wherein said lip extender comprises a pair of dual-sided lip holders at each extender end, each said lip holder engageable with the lips at a side of the mouth, so that the user can extend either cheek without changing the hand in which said handle is held.

2. The cheek retractor of claim 1 wherein said lip extenders are separated by a pair of elongated bridges, such that said work area is defined by said bridges and said lip extenders are connected to said bridges.

3. A cheek retractor comprising a generally oval lip extender surrounding a generally oval work area, said lip extender having a pair of ends at either elongated end of said oval work area, either of said extender ends engageable with the lips, and a handle extending from one end of the lip extender, such that when a force is exerted by the holder on the handles, one of the extender ends engages a lip and draws the cheek away from the mouth and toward the back of the head to expose the teeth at the work are wherein said lip extender comprises a pair of dual-sided lip holders at each said extender end, each said lip holder engageable with the lips at a side of the mouth, so that the user can extend either cheek without changing the hand in which said handle is held.

4. The cheek retractor of claim 3 wherein said lip extenders are separated by a pair of elongated bridges, such that said work area is defined by said bridges and said lip extenders connected to said bridges.

5. A cheek retractor comprising a generally oval lip extender surrounding a generally oval work area, said lip extender having a pair of ends at either end of said oval work area, either of said ends engageable with the lips and handle extending from one end of the lip extender, such that when a force is exerted by the holder on the handle, one of the ends engages a lop and draws the cheek away from the mouth to expose the teeth at the work area, said lip extender further comprising a pair of dual-sided lip holders at each said extender end, each said lip holder engageable with the lips at a side of the mouth, so that the user can extend either cheek without changing the hand in which said handle is held.

6. The cheek retractor of claim 5 wherein said lip extenders are separated by a pair of elongated bridges, such that said work area is defined by said bridges and said lip extenders are connected to said bridges.

* * * * *

UNITED STATES PATENT AND TRADEMARK OFFICE
CERTIFICATE OF CORRECTION

PATENT NO. : 4,971,557

DATED : November 20, 1990

INVENTOR(S) : Patrick E. Martin

It is certified that error appears in the above-identified patent and that said Letters Patent is hereby corrected as shown below:

Column 3, line 8 "are" should be "area".

Column 4, line 7 "lop" should be "lip".

Signed and Sealed this

Fourteenth Day of July, 1992

Attest:

DOUGLAS B. COMER

*Attesting Officer*  *Acting Commissioner of Patents and Trademarks*